United States Patent [19]
Cederstrand et al.

[11] Patent Number: 5,512,757
[45] Date of Patent: Apr. 30, 1996

[54] SPECTROPHOTOMETER AND OPTICAL SYSTEM THEREFOR

[75] Inventors: Carl N. Cederstrand, Brea; Sharam M. Salimian, Westminster; Rolf W. Siemon, Brea, all of Calif.

[73] Assignee: Rosemount Analytical, Inc., La Habra, Calif.

[21] Appl. No.: 863,830

[22] Filed: Apr. 6, 1992

[51] Int. Cl.$^6$ .................................................. G01N 21/33
[52] U.S. Cl. ......................... 250/373; 250/345; 250/346; 356/437
[58] Field of Search ................................... 250/373, 343, 250/344, 345, 346; 356/437

[56] References Cited

U.S. PATENT DOCUMENTS

| | | | |
|---|---|---|---|
| 2,573,870 | 11/1951 | Pfund | 250/343 |
| 3,032,654 | 5/1962 | Fay et al. | 250/373 |
| 3,806,727 | 4/1974 | Leonard et al. | 250/373 |
| 3,916,195 | 10/1975 | Burch et al. | 250/345 |
| 3,947,685 | 3/1976 | Meinel | 250/373 |
| 3,969,626 | 7/1976 | Saltzman | 250/373 |
| 4,180,734 | 12/1979 | Gedeon | 250/373 |
| 4,678,917 | 7/1987 | Helms et al. | 25/373 |

FOREIGN PATENT DOCUMENTS 2245058  12/1991  United Kingdom .................. 356/437

*Primary Examiner*—Carolyn E. Fields
*Attorney, Agent, or Firm*—John E. Vanderburgh

[57] ABSTRACT

The photometer of the present invention includes an optical system in which an emission beam generated by pulsed ultra violet radiation from a source is split into a sample beam and a reference interference beam by spectrally selective mirrors arranged in series. These mirrors reflect a beam having a wavelength range corresponding to an absorption wavelength of the gas to be detected onto one solid state detector and to pass a beam to a second spectrally selective mirror where a beam having second range of wave lengths corresponding to an interfering gas is reflected onto a second solid state detector. This second beam serves to measure the interfering gas and also as an imperfect reference channel. In a preferred embodiment the radiation from the source is split prior to entering the sample cell. One beam is directed through an optical path which avoids the sample cell but which is otherwise identical to the optical path described above, including series arranged spectrally selective mirrors to be further split the beam into two beams having wavelength ranges corresponding to the wavelength ranges of the sample and reference gases. These beams are directed to solid state detectors and the signals derived therefrom are combined with a second set of similar signals derived from the sample and reference beams which have passed through the sample cell.

12 Claims, 4 Drawing Sheets

SPECTROPHOTOMETER AND OPTICAL SYSTEM THEREFOR

FIELD OF THE INVENTION

The invention relates to an ultra violet photometer having improved signal to noise ratio and improved discrimination.

BACKGROUND

Optical systems for UV photometers often times provide very low signals. This is particularly true when interference filters are employed as the wavelength determining devices. Ultra violet interference filters typically display peak transmissions of about 10%. This results in a signal loss of about 90% when ultra violet radiation passes through an interference filter. In order to operate at these low signal levels, ultra violet optical systems employing interference filters must generally incorporate very sensitive detectors, normally expensive photomultipliers which also require high voltage power supply. In addition, the sensitivity of ultra violet photometers is adversely affected by any instability (noise) arising from the emission source. Ultra violet emission sources are generally gas discharge lamps, all of which suffer to a greater or lesser degree from arc instability. Instrument drift is also encountered as a result of the accumulation of contaminates on the sample cell walls and windows. Also, spectral overlap is considerably more severe in the ultra violet than in the infrared and thus ultra violet photometers are generally characterized by low discrimination ratios and thus may have difficulty in distinguishing between various constituents in a sample gas. Finally, if a sector disc is employed for chopping of the beam, attendant problems of motor stability, mechanical noise and bearing longevity are encountered.

SUMMARY OF THE INVENTION

It is an object of the present invention to provide an improved ultra violet photometer for the detection of low concentration constituents in gaseous samples.

Another object of the present invention is to provide an improved optical system for photometers which can operate in the ultraviolet region without interference filters and the attendant reduction in signal strength caused thereby.

Another object of the invention is to provide an improved ultra violet photometer which measures two constituents and is thus a dual output instrument.

Yet another object of the present invention is to provide an improved ultra violet photometer having improved optical and electronic systems that compensate for arc instability and hence reduce noise and drift in the instrument output.

Still another object of the invention is to provide an ultra violet photometer that is less sensitive to the effects of deposits in the sample cell.

Yet still another object of the invention is to provide a photometer having an improved discrimination ratio.

These and other features and advantages are achieved by the photometer of the present invention in which an emission beam generated by pulsed ultra violet radiation from a source is split into a sample beam and a reference interference beam by spectrally selective mirrors arranged in series. These mirrors reflect a beam having a wavelength range corresponding to an absorption wavelength of the gas to be detected onto one solid state detector and to pass a beam to a second spectrally selective mirror where a beam having second range of wave lengths corresponding to an interfering gas is reflected onto a second solid state detector. This second beam serves to measure the interfering gas and also as an imperfect reference channel.

Utilizing the spectrally selective mirrors permits both splitting of the beam and selecting wavelengths with a very low loss in signal. It also contributes to raising the signal levels so that the signals reaching the detectors are adequate to permit the use of less expensive solid state detectors.

In another embodiment of the invention the radiation from the source is split prior to entering the sample cell. One beam is directed through an optical path which avoids the sample cell but which is otherwise identical to the optical path described above, including series arranged spectrally selective mirrors to be further split the beam into two beams having wavelength ranges corresponding to the wavelength ranges of the sample and reference gases. These beams are directed to solid state detectors and the signals derived therefrom are combined with a second set of similar signals derived from the sample and reference beams which have passed through the sample cell. The use of two identical sets of detectors and spectrally reflective mirrors provides a proper reference beam signal which exactly cancels source noise and thus allows this photometer to make full scale measurements in the parts per million range.

In its preferred form, the optical system of this invention includes a collector mirror which focuses and directs the beam from the source through the sample cell in a manner to avoid contact with the walls of the sample cell. Upon emerging from the sample cell, the beam impinges on to a reducing mirror. This reducing mirror then reflects and focuses the beam on the series arranged spectrally selective mirrors and thence to the detectors.

In yet another embodiment of the invention the optical system can be adapted for the measurement of a second component such as $NO_2$ in a gaseous stream by utilizing a third spectrally selective mirror and a third detector in the optical path.

Other objects, advantages and features of the present invention will become apparent from the following detailed description taken in conjunction with the drawings.

DETAILED DESCRIPTION OF THE INVENTION

The system of this invention provides a stable, uniformly illuminated and sharply defined image on the detectors. Use of series arranged spectrally selective mirrors requires lower operating power and the need for interference filters. The use of the less expensive spectral mirrors and solid state detectors lowers the cost of the optical system and contributes to a stronger signal which thus allows the instrument to be operated at levels of increased sensitivity. Interference filters for use in the ultraviolet, have peak transmissions between 10% to 15% which thus reduces signal strength by 85% to 95%. The elimination of the interference filters and their replacement with spectral mirrors aids in increasing the signal strength at the detectors and allows for the use of much less expensive solid state detectors, such as silicon solar cells rather than the more expensive photomultiplier detectors that are normally required for low signal operation.

In the following detailed description the invention will be described in connection with a photometer configured for measurement of $SO_2$ in the ultraviolet region of the electromagnetic spectrum although it will be understood that the optical system of this invention is equally applicable to photometers which operate in other regions of the spectrum, such as the visible and infrared regions.

Figure 1:
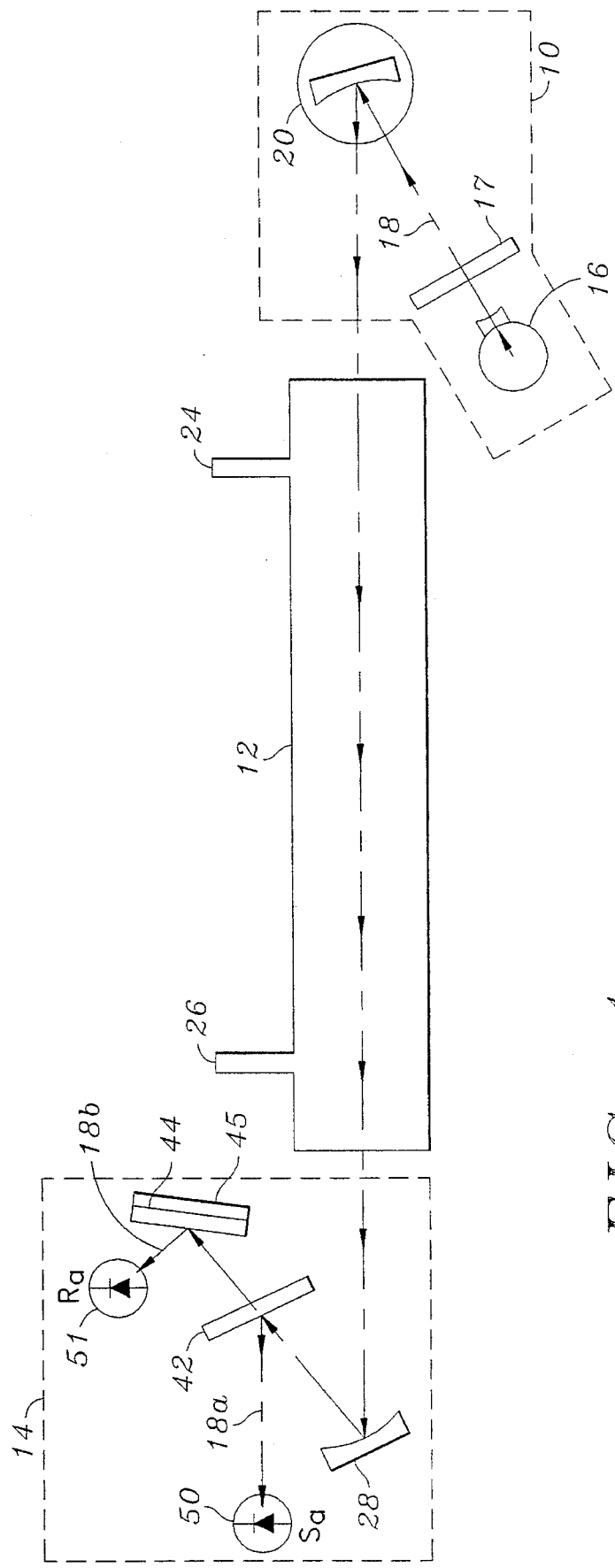
FIG. 1 is a schematic representation of the optical system in accordance with one embodiment of the invention.

Referring to FIG. 1 the optical system of the photometer comprises three general groups, a source group 10, a conventional sample cell 12 and a detector group 14. The emission source group 10 includes a deuterium lamp 16 for the emission of a beam 18 of ultraviolet radiation. In the preferred embodiment the deuterium lamp 16 is pulsed so that the emission radiation is pulsed. Although it is not preferred, a sector disc and motor (not shown) can be imposed somewhere in the light path for the mechanical chopping of beam 18 in lieu of pulsed lamp 16.

In the embodiment illustrated in FIG. 1, a spectrally selective cutoff mirror 17 is disposed immediately in the emission path of the lamp 16 for reflecting radiation of wavelengths shorter than 265 nm and transmitting only wavelengths longer than 265 nm. A spherical collecting mirror 20 is positioned in the optical path adjacent to filter 17 for collecting the filtered radiation from lamp 16 and focusing it on mirror 28. As will be discussed in more detail hereinafter, the collector mirror 20 is situated so that its optical axis is rotated in a clockwise direction from its incident radiation 18.

The sample cell 12 is provided with UV transparent entrance and exit windows (not shown) as is conventional. The sample cell 12 is also provided with an inlet 24 and outlet 26 for the flow of a sample gas through the sample cell.

Focusing the emission beam 18 with the collecting mirror 20 allows the beam to pass through the sample cell 12 with little contact with the walls of the sample cell. In this manner the effect of contamination on the sidewalls of the cell 12, which produces a reduction in signal strength and an increase in drift, is greatly reduced. In addition, by use of a focused beam, the material from which the sample cell 12 is constructed is not a factor with respect to absorbance of the radiation and in the embodiment of the invention discussed herein the sample cell 12 can be fabricated from ordinary glass tubing.

The focused beam 18 leaves the sample cell 12 and is directed towards detector 50 and 51 by means of a second spherical mirror, referred to as the reducing mirror 28. The reducing mirror 28 is positioned so that its optical axis is counterclockwise to its incident beam 18 of radiation.

The detector group 14 includes a first and a second spectrally selective mirror, 42 and 44 respectively, disposed in series along the beam reflected by the reducing mirror 28. Each spectral mirror reflects a beam of selected wavelengths to a corresponding solid state detector, 50 and 51. In this manner the first spectrally selective mirror 42 serves to spectrally split the beam 18 into two beams of different wavelengths. The reflected beam 18a serves as the sample beam and is reflected to the solid state detector 50. Those wavelengths of beam 18 that are transmitted through spectral mirror 42 impinge on the second spectrally selective mirror 44. The second spectral mirror 44 reflects a different band of wavelengths, beam 18b, referred to as the interferant/reference beam, to the second solid state detector 51. That radiation that is transmitted through mirror 44 is absorbed by an absorbent coating 45 that has been applied to the back of mirror 44.

Signals from the detectors 50 and 51 are suitably amplified and the sample signal is subtracted from the interferant/reference signal by appropriate circuitry. Eventually a signal is obtained which is proportional to the concentration of the sample gas in the sample cell. The resultant signal is sent to a suitable read-out and/or recording device, also not shown. Any of the well known photometer circuits for subtracting the sample and reference signals and for reading and recording the resultant output may be used to process the output signals of the detectors 50 and 51.

As illustrated in FIG. 1 the collecting mirror 20 and the reducing mirror 28 are introduced into the optical path to focus beam 18 and to stabilize the detector signal. The collecting mirror 20 subtends a significant solid angle of radiation emitted from the lamp 16 and forms a real image of the radiating plasma contained in lamp 16 on the reducing mirror 28. The reducing mirror 28 in turn forms a reduced real image of the collecting mirror 20 on each detector. As mentioned, the focused beam 18 enters and exits the sample cells without making any substantial contact with the sidewalls of the sample cells thus eliminating problems due to contamination on the sample cell 12 sidewalls.

The focusing mirrors 20 and 28 serve to provide a signal increase at the detectors of at least two orders of magnitude greater than that obtained with a comparable non-focused system. For example, in the embodiment illustrated, an aperture stop is defined by the collector mirror 20 which is located approximately 3 inches from the source of UV radiation. Were the focusing mirrors not included in the optical system, the aperture stop then is defined at each of the detectors 50 and 51, both of which are located about 20 inches from the source. Accordingly, the use of the mirrors 20 and 28 in the optical system of the present invention are preferred, so that loss of signal energy is kept to a minimum. It is the high detector signal level which allows the use of less expensive solid state detectors.

A problem often encountered in photometer optical systems is that of off-axis aberrations (coma and astigmatism). Such aberrations result in a spread out or blurred image. A blurred image that spills over the edge of the detector has the potential for making the optical bench sensitive to vibration and/or drift when any optical element moves. The before mentioned off-axis aberrations are reduced by rotating the optical axis of the collecting mirror 20 clockwise from its incoming rays and the reducing mirror 28 counter-clockwise from its incoming rays. The angles of rotation are equal and the senses of rotation are opposite. By maintaining these symmetric conditions with mirrors of the same focal length, the off axis aberration in the optical system tend to cancel.

Figure 2:
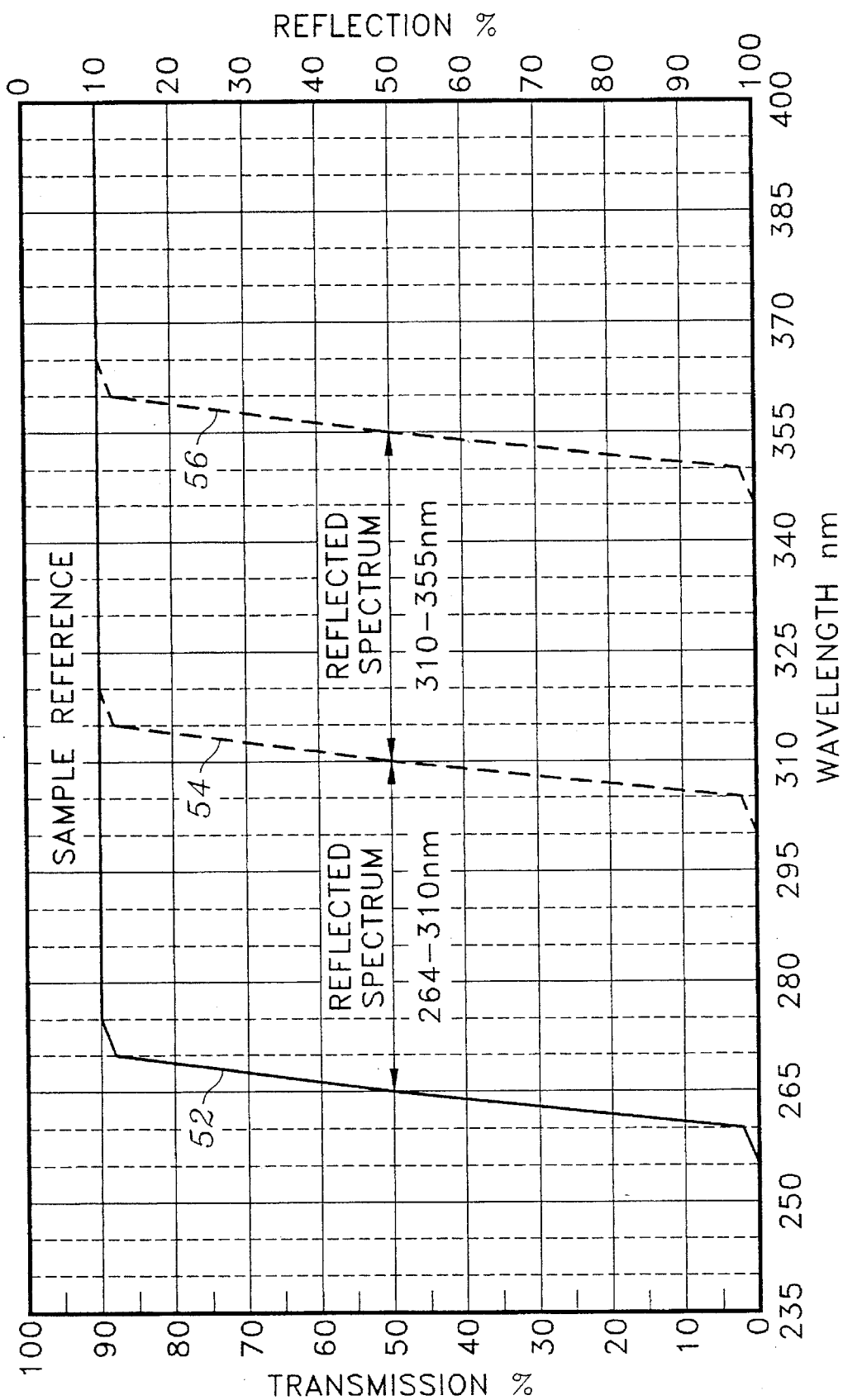
FIG. 2 is a plot of reflection and transmission verses wave length for the spectrally reflective mirrors of FIG. 1.

FIG. 2 shows the wavelengths of the sample beam 18a and reference beam 18b generated for the measurement of $SO_2$ in a gaseous sample such as air. The spectrally selective cutoff mirror 17 transmits all radiation from the lamp 16 having wavelengths longer than 265 nm. The spectrally selective mirror 42 is designed to reflect incident radiation of wavelengths shorter than 310 nm and to transmit radiation having wavelengths longer than 310 nm. Similarly the spectrally selective mirror 44 reflects radiation at wavelengths shorter than 355 nm and transmits incident radiation having wavelengths longer than 355 nm. As illustrated by FIG. 2, curve 52 displays the percent transmission and reflection versus wave length for the spectrally selective mirror 17. The percent reflection is directly inverse to percent transmission. Curve 54 is a similar plot of percent transmission and reflection versus wavelength for the spectrally selective mirror 42 while curve 56 is the same plot for the spectrally selective mirror 44. The area between curve 52 and curve 54 determines the spectral region of the sample beam. It is generated by those wavelengths that pass through the first spectrally selective mirror 17 and are then reflected by spectrally selective mirror 42. As illustrated the sample beam consists of wavelengths between 265 nm and 310 nm. A strong absorption band for $SO_2$ occurs within this range of wavelengths. An absorption band for $NO_2$, the primary interferant in the determination of $SO_2$, also occur in this wavelength range and thus effects the output signal of the detector 50. The area between curve 54 and curve 56 represents the wavelength range reflected by spectrally selective mirror 44. This wavelength range is used for the combined interferant and reference beam 18b. Absorption bands for $NO_2$ also occur in this range of 310 nm to 355 nm. The signals generated by the absorption of $NO_2$ in the sample and reference beam are made equal using a digital controlled resistor (Interference adjustment) to eliminate the effect of the $NO_2$ in the sample signal and thus determine at the true concentration of $SO_2$ in the sample gas. Such resistors and their function are well known in the art and do not per se form a part of this invention.

While the foregoing description is in connection with the determination of $SO_2$ where $NO_2$ is an interfering substance, it will be understood the system is equally effective for the determination of other gases which absorb at different wavelengths. This is readily accomplished by the use of spectrally selective mirrors which transmit and reflect within the wavelength range of the absorption bands of the gases of interest. Spectrally selective mirrors do not, per se, form a part of this invention and their transmittance and reflectance properties are known in the art.

Figure 3:
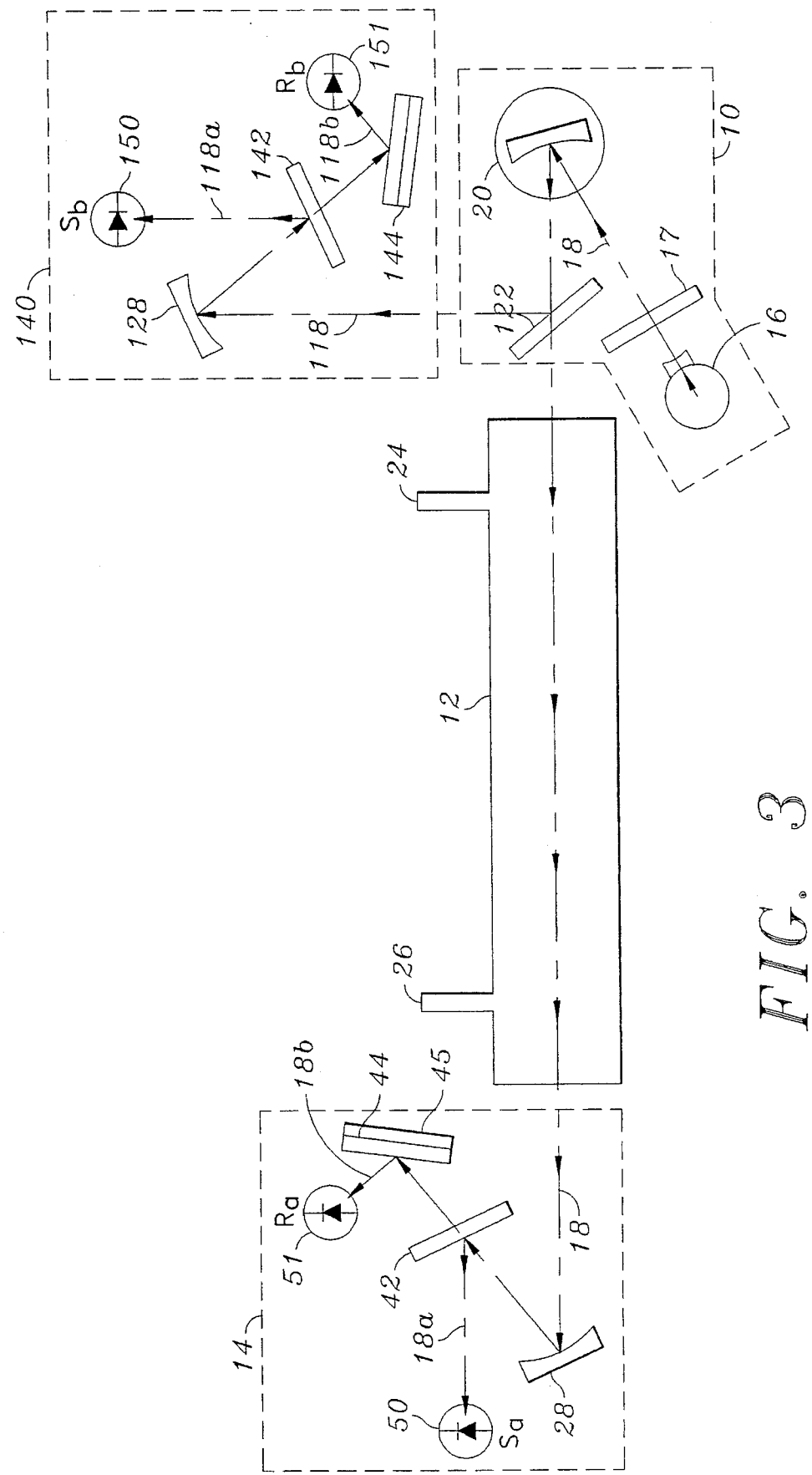
FIG. 3 is a schematic representation of the optical system in accordance with a preferred embodiment of the invention.
Figure 4:
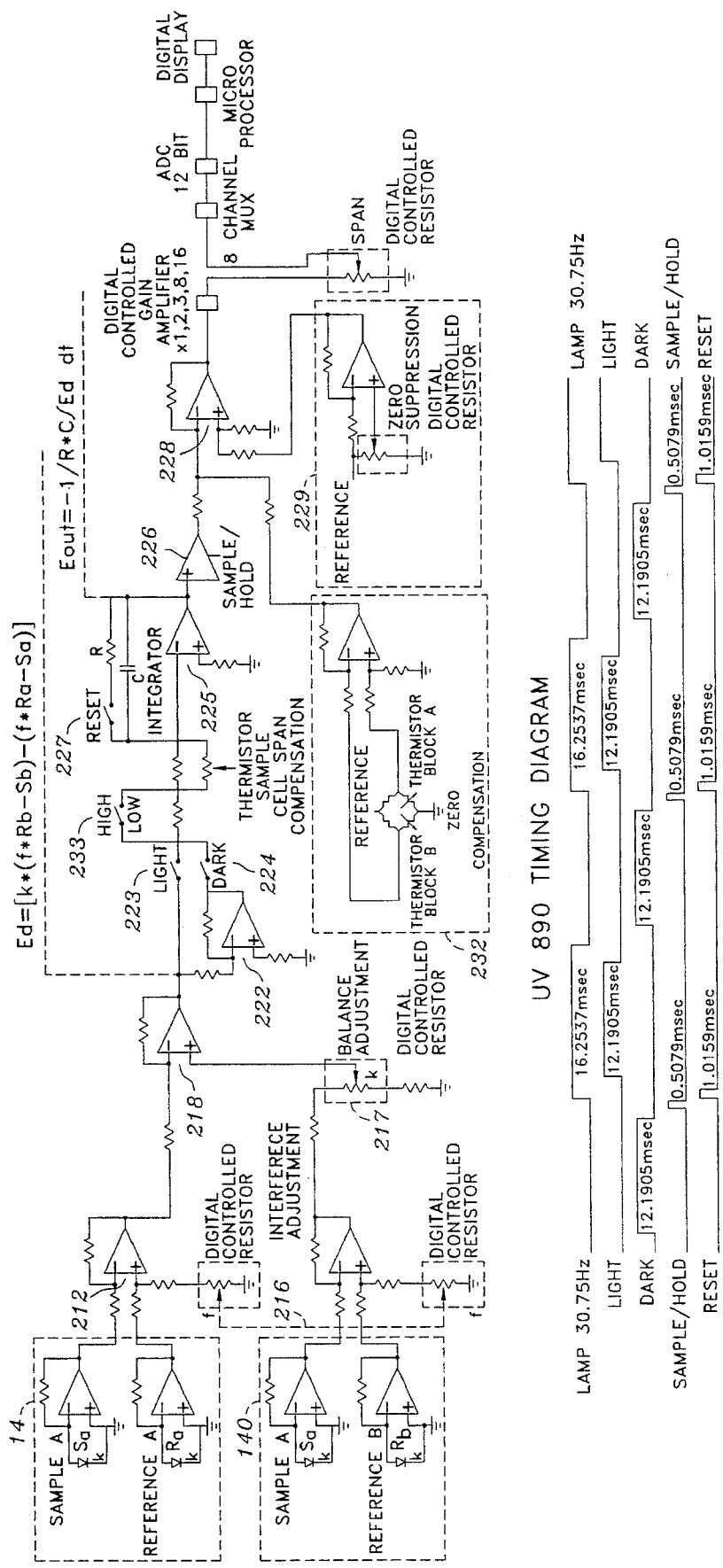
FIG. 4 is a schematic diagram of the circuitry employed with the optical system of FIG. 3.

Referring to FIGS. 3 and 4, in which like reference numbers designate like parts, a preferred embodiment of the invention is illustrated in which the optical system and electronics are extended to more exactly compensate for source fluctuations and drift. The system is capable of measuring $SO_2$ in the region of less than 10 ppm full scale as compared to the optical bench described above in connection with FIG. 1, which is limited to about 200 ppm full scale. The optical system includes the source group 10, the sample cell 12 and the detector group 14 which functions as described above in connection with FIG. 1. The spectral mirrors have the same spectral properties as illustrated in FIG. 2. An additional detector group 140 is added for measuring the same wavelength ranges as the detector group 14 for a portion of the beam 18 which bypasses the sample cell 12. The comparison group 140 consists of spectrally selective mirrors 142 and 144 which are arranged in series along the optical path of a beam 118 split by a conventional beam splitter 122 positioned between the collecting mirror 20 and the sample cell 12. The beam splitter 122 is of any conventional design and good results have been achieved using a metallic splitter having a surface area which transmits 50% of the incident radiation. As is the case for the detector group 14 adapted for the detection and measurement of $SO_2$, spectrally selective mirror 142 reflects radiation in the range of 265 mn to 310 nm and spectrally selective mirror 144 reflects radiation in the range of 310 nm to 355 nm. Each of the mirrors 142 and 144 is positioned to reflect a beam to a solid state detector 150 and 151 respectively.

As shown in FIG. 4, a differential amplifier 212 receives the signals from the solid state detectors of the detector group 14. A similar differential amplifier 214 receives signals from the detectors of detector group 140. The digitally controlled resistors 216 are ganged together and electrically control the magnitude of the interferant/reference signals from the detector groups 14 and 140 which are fed into the differential amplifiers 212 and 214. The setting of the digitally controlled resistor 216 provides electrical compensation for interferant gases like $NO_2$. The resistor is adjusted so that zero output is obtained when the interfering gas is flowing through the sample cell 12.

A differential amplifier 218 receives the output of the differential amplifier 212 and 214 and its output is the difference between the outputs of the differential amplifiers 212 and 214. A digitally controlled resistor 217 is used to balance the instrument to zero when a nonabsorbent gas flows through the sample cell 12. The output of amplifier 218 is fed to an integrator 225 via the "light" switch 223 (when the lamp is on) and the inverted signal (222) of 218 is fed to an integrator 225 via the "dark" switch 224 (when the lamp is off). This allows the electronic to subtract the detector dark currents from the detector light currents. After completion of the "light" and "dark" cycle the sample and hold circuit 226 picks up the integrated signals. The integrator is reset to zero with the "reset" switch 227 in preparation for the next "light" and "dark" cycle. A summing amplifier 228 receives the output of the sample and hold circuit 226 as well as the signal from the temperature compensation unit 232 and the zero suppression circuit 229 to provide the final output signal which is directly related to the concentration of the substance being measured. A "high/low" switch 233 is used to attenuate the input signal for the integrator 225 for high concentration measurements. The operation of this photometer will be described in a configuration suitable for detecting $SO_2$ in the presence of $NO_2$. The lamp 16 emits pulses of ultraviolet radiation which first pass through the cutoff mirror 17 which reflects wave lengths shorter than 250 nm and transmits wavelengths longer than 265 nm. The transmitted pulses of ultra violet radiation are then focused by the mirror 20 to form a focused beam that is directed through the sample cell 12. The sample gas is admitted into the sample cell 12 through the inlet 24 and is exhausted from the sample cell through outlet 26. Before entering the sample cell the focused beam is intercepted by a beam splitter 122 where approximately 50% of the focused beam is directed to the comparison group of detectors 140. The remainder of the focused beam passes through the sample cell and finally forms a real image on the reducing mirror 28. The beam from the reducing mirror is directed to the spectrally selected mirror 42 which has been designed to reflect wave lengths shorter than 310 nm. Since the cutoff mirror 17 transmits only those wave lengths longer than 265, the wave length range from the spectrally selected mirror 42 is between 265 and 310 nm. The signal from the solid state detector 50 thus is representative of the absorption of radiation by $SO_2$ as well as the primary interferant gas $NO_2$. The spectrally selective mirror 44 reflects a beam in the range of 310 nm to 355 nm. This is in the range of additional absorption bands of $NO_2$ but none of $SO_2$. The signal from the solid state detector 51 is thus representative of $NO_2$ present in the sample gas. The signals from the solid state detectors 50 and 51 are referred to as the sample signal and interferant signal respectively. The difference between these two signals in determined by differential amplifier 212 whose output that is thus related to the concentration of the $SO_2$ in the sample gas compensated for $NO_2$ interference.

The comparison group of detectors 140, operating in the same fashion as the detector group 14, respond to that half of the split beam, which has not passed through the sample cell 12. The output from the solid state detectors 150 and 151 are directed to the differential amplifier 214 for subtraction of the signals. The outputs of the differential amplifiers 212 and 214 are then directed to the differential amplifier 218 which then subtracts the signals of the detector group 14 from that of the comparison group 140. In this manner, both the sample and interferant signals are corrected for source noise and drift and an extraordinarily stable signal is obtained which is related only to $SO_2$ concentration in the sample gas. While this invention has been described in conjunction with an optical system which splits the emission beam 18 into a reference beam 18a and a sample beam 18b, it is clear that an additional signal channel could be added by utilizing the long wave length radiation presently transmitted through the second spectrally selective mirror 44 (see FIG. 1) and now absorbed by the black paint 45 on its back surface. A third band pass can thus be added by removing the black paint and adding another spectrally selective mirror and detector in the manner described for the measurement in a third wavelength range.

From the foregoing it will be seen that the optical system of the present invention eliminates the necessity for the use of interference filters which, particularly in the ultra violet ranges, transmit very poorly and can result in an energy loss of as much as 90%. By the use of series positioned spectrally selective mirrors the beam is split into two or more bands of wavelengths. The use of the spectrally selective mirrors considerably reduces the component cost of an ultra violet photometer and when used in conjunction with the spherical mirrors as described herein the intensity of the radiation reaching the detectors is sufficient to permit the use of solid state detectors rather than the more expensive photo-multipliers which are normally required for UV photometers.

While the foregoing has been described in connection with an embodiment which is an ultraviolet photometer for the measurement of $SO_2$, it will be understood that by suitable variations in the reflective and transmitted wave lengths of the spectrally selective mirrors that other gaseous components can be measured.

As will be understood by those skilled in the art, various arrangements other than those described in detail in the specification will occur to those persons skilled in the art, which arrangements lie within the spirit and scope of the invention. It is therefore to be understood that the invention is to be limited only by the claims appended hereto.

Having described the invention I claim:

1. In a spectrophotometer of the type having a sample cell for containing sample to be analyzed, an emission source for directing radiation through said sample cell, filter means in the path of said radiation for eliminating wavelengths shorter than a designated wavelength, detectors for detecting radiation of selected wavelengths emitted from said sample cell and for producing an electronic signal in response to the detected radiation and means for measuring said electronic signal from said detectors as an indicator of the quantities of sought for component in said sample, the invention comprising:

a. at least a first and a second spectrally selective mirror serially positioned in the path of a beam of radiation emitted from said sample cell;

b. said first spectrally selective mirror being selected to reflect to a first detector a first band of wavelengths having a range at least encompassing the absorption spectrum of a first gas being detected and to transmit remaining wavelengths to said second spectrally selective mirror;

c. said second spectrally selective mirror being selected to reflect a second band of wavelengths different from said first band and having a range encompassing a second gas to a second detector; and d. means for integrating said electronic signal from said first and said second detectors;

thereby to obtain an output signal directly related to the concentration of one of said first and second gas.

2. The spectrophotometer of claim 1 further including a third detector disposed to detect radiation within said band of wavelengths transmitted by said second spectrally selective mirror.

3. The spectrophotometer of claim 1 further including a collector mirror for reflecting and focusing said beam from said emission source through said sample cell to avoid contact with the walls of the sample cell.

4. The spectrophotometer of claim 3 wherein further including a reducing mirror in the path of the emitted beam from said sample cell, said reducing mirror forming a real image of said collector mirror which is reduced in size on said first spectrally selective mirror.

5. The spectrophotometer of claim 4 wherein said collector mirror and said reducing mirror are short focus spherical mirrors, the optical axis of said collector mirror being rotated clockwise with respect to said collector mirror and the optical axis of said reducing mirror being rotated counterclockwise with respect to said reducing mirror, the angle of rotation of said optical axes of said collector and said reducing mirrors being equal.

6. The spectrophotometer of claim 1 wherein said emission source is pulsed.

7. The spectrophotometer of claim 1 wherein said emission source is a deuterium lamp which emits radiation in the ultra violet range.

8. The spectrophotometer of claim 1 wherein said filter means consists of a spectrally selective cutoff mirror disposed between said emission source and a collector mirror, said cut off mirror transmitting only wavelengths in excess of about 260 nm.

9. The spectrophotometer of claim 8 wherein said first spectrally selective mirror reflects wavelengths of less than about 305 nm and transmits radiation having a wavelength in excess of about 315 nm and said second spectrally selective mirror reflects less than about 350 nm and transmits radiation having a wavelength in excess of about 360 nm.

10. The spectrophotometer of claim 9 wherein the reflected beam from said first spectrally selective mirror has a wavelength range of between about 260 nm and about 315 nm and the reflected beam from said second spectrally selective mirror has a wavelength range of between about 315 nm and about 360 nm.

11. An emission spectrophotometer comprising a source group, a sample cell, a detector group and a comparison group, said source group including an emitter of ultra violet radiation, filter means in the path of said radiation for eliminating wavelengths shorter than a designated wavelength and a beam splitter dividing the emitted radiation into a first and a second beam, said first beam being directed through said sample cell and said second beam being directed to said comparison group, said detector group including a first and a second spectrally selective mirror disposed in series along the optical axis of said first beam, said first spectrally selective mirror reflecting incident source group radiation from said sample cell below a selected wavelength to a solid state detector and transmitting radiation in excess of said selected wavelength, said second spectrally selective mirror reflecting transmitted radiation from said first spectrally selective mirror below a second selected wavelength to a solid state detector, said comparison group including a first and a second spectrally selective mirror disposed in series along the optical axis of said second beam, said first and second spectrally selective mirrors of said comparison group corresponding in optical characteristics to said first and second spectrally selective mirrors of said detector group, and circuit means for integrating the solid state detector signals thereby to derive a signal directly related to the quantity of a gas being detected which has been compensated for interferant gases and source aberrations.

12. In a spectrophotometer of the type having a sample cell for containing sample to be analyzed, an emission source for directing radiation through said sample cell, at least two detectors for detecting radiation of different selected wavelengths emitted from said sample cell and for producing an electronic signal in response to the detected radiation and means for measuring and integrating the electronic signal from each detector as an indicator of the quantities of sought for component in said sample, the invention comprising an improved optical system including:

a. a collecting mirror adjacent said source forming a magnified real image of said emission source, said collecting mirror having the optical axis thereof rotated clockwise with respect to said collecting mirror so that emitted radiation from said source is first focused by said collecting mirror and reflected as a focused beam through said sample cell;

b. a reducing mirror in the path of the emitted beam from said sample cell, the optical axis thereof being rotated counterclockwise with respect to said reducing mirror, said reducing mirror forming a real image of said collecting mirror which is reduced in size; whereby the image reflected by said reducing mirror is a stable, uniformly illuminated and sharply defined image of said emission source.

\* \* \* \* \*